(12) United States Patent
Bergman et al.

(10) Patent No.: US 6,377,832 B1
(45) Date of Patent: *Apr. 23, 2002

(54) SYSTEM AND METHOD FOR ANALYZING A MEDICAL IMAGE

(75) Inventors: Harris L. Bergman, Smyrna; David N. Ku, Atlanta, both of GA (US)

(73) Assignee: Georgia Tech Research Corporation, Atlanta, GA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/272,862

(22) Filed: Mar. 19, 1999

Related U.S. Application Data

(60) Provisional application No. 60/078,811, filed on Mar. 20, 1998.

(51) Int. Cl.⁷ .................................................. A61B 5/05
(52) U.S. Cl. .......................... 600/408; 600/410; 128/925
(58) Field of Search .................................. 600/408, 410, 600/411, 425, 427; 128/920, 922, 923, 924, 925

(56) References Cited

U.S. PATENT DOCUMENTS

| | | | | |
|---|---|---|---|---|
| 4,849,697 A | * | 7/1989 | Cline et al. | 324/306 |
| 5,150,292 A | * | 9/1992 | Hoffmann et al. | 600/420 |
| 5,190,744 A | * | 3/1993 | Rocklage et al. | 424/9 |
| 5,352,979 A | * | 10/1994 | Conturo | 324/307 |
| 5,377,681 A | * | 1/1995 | Drane | 600/419 |
| 5,638,823 A | * | 6/1997 | Akay et al. | 600/504 |
| 5,685,305 A | * | 11/1997 | Moonen et al. | 600/419 |
| 5,872,861 A | * | 2/1999 | Makram-Ebeid | 382/130 |

OTHER PUBLICATIONS

A. Armoni, "Use of Neutral Networks in Medical Diagnoses," M.D. Computing, vol. 15, No. 2, 1998, pp. 100–104.
Perman, et al., "Artifacts from Pulsatile Flow in MR Imaging," Journal of Computer Assisted Tomography, vol. 10, No. 3, 1986, pp. 475–483.
Downing, et al, "Flow Through a Compliant Stenotic Artery," Advances in Bioengineering, vol. 26, 1993, pp. 137–140.
Barnett, et al., "Beneficial Effect of Carotid Endarterectomy in Symptomatic Patients with High–Grade Carotid Stenosis," The New England Journal of Medicine, vol. 325, No. 7, Aug. 15, 1991, pp. 445–453.
Scarselli, et al., Universal Approximation using Feedforward Neural Networks: a Survey of Some Existing Methods, and Some New Results, Neural Networks, vol. 11, No. 1, 1998, pp. 15–37.
Saloner, et al., "MRA Studies of Aterial Stenosis: Improvements by Diastolic Acquisition," MRM 31 1994, pp. 196–203.

(List continued on next page.)

*Primary Examiner*—Brian L. Casler
(74) *Attorney, Agent, or Firm*—Thomas, Kayden, Horstemeyer & Risley LLP

(57) ABSTRACT

Disclosed is a system and method for determining a severity of a stenosis in a blood vessel depicted in a magnetic resonance imaging (MRI) data set. The system comprises a neural network configured to calculate the severity of the stenosis in the blood vessel based upon a number of input parameters, and the input parameters including at least one characteristic of a signal void associated with the stenosis in the MRI data set. The input parameters may include, for example, a flow rate of blood through the blood vessel, a length of a longitudinal axis of the signal void, and an average image intensity along the longitudinal axis of the signal void as well as other input parameters.

80 Claims, 7 Drawing Sheets

OTHER PUBLICATIONS

Scott Sheppard, MS, "Basic Concepts in Magnetic Resonance Angiography," Radiologic Clinics of North America, vol. 33, No. 1, Jan. 1995, pp. 91–112.

Masaryk, et al., "Carotid Bifurcaction: MR Imaging Work in Progress," Radiology, vol. 166, No. 2, Feb. 1988 pp. 461–466.

Tsuruda, et al., "Artifacts Associated with MR Neuroangiography," Americal Society of Neuroadiology, ANJR: 13, Sep./Oct. 1992, pp. 1411–1422.

Young, et al., "Flow Characteristics in Models of Arterial Stenoses–I. Steady Flow," J. Biomechanics, 1973, vol. 6, No. 4–E, pp. 395–410.

Kim, et al., Experimental Measurements of Turbulence Spectra Distal to Stenoses, J. Biomechanics, 1974, vol. 7, pp. 335–342.

C.Clark, "Turbulent Velocity Measurements in a Model of Aortic Stenosis," J. Biomechanics, 1976, vol. 9, pp. 677–687.

Soh, et al., "Laminar Entrance Flow in a Curved Pipe," J. Fluid Mech., 1984, vol. 148, pp. 109–135.

Gatenby, et al., "Mapping of Turbulent Intensity by Magnetic Resonance Imaging," Journal of Magnetic Resonance, Series B 104, 1994, pp. 119–126.

Oshinski, et al., Turbulent Fluctuation Velocity: The Most Significant Determinant of Signal Loss in Stenotic Vessels, MRM 33: 193–199, 1995.

Siegel, et al., "Computational Simulation of Turbulent Signal Loss in 2D Time–of–Flight Magnetic Resonance Angiograms," MRM 37:609–614, 1997.

Kuethe, et al., NMR Signal Loss from Turbulence: Models of Time Dependence Compared with Data, The American Physical Society, 1995, pp. 3252–3261.

Gatenaby, et al., "Characterization of Turbulent Flows by NMR Measurements with Pulsed Gradients," Journal of Magnetic Resonance, Series A 110, 1994, pp. 26–32.

Gao, et al., "Turbulent Flow Effects on NMR Imaging: Measurement of Turbulent Intensity," Med. Phys. vol. 18 No. 5, Sep./Oct. 1991, pp. 1045–1051.

Rittgers, et al., "Velocity Profiles in Stenosed Tube Models Using Magnetic Resonance Imaging," Transactions of the ASME, vol. 110, Aug. 1988, pp. 180–184.

Tyen, et al., "MR Imaging of Flow Through Tortuous Vessels: A Numerical Simulation," MRM 31:184–195, (1994).

Dean O. Kuethe, "Measuring Distributions of Diffusivity in Turbulent Fluids with Magnetic–Resonance Imaging," The American Physical Society, vol. 40, No. 8, pp. 4542–4551.

Urchuk, et al., "Mechanisms of Flow–Induced Signal Loss in MR Angiography," JMRI 1992; 2:453–462.

Spielmann, et al., "Appearance of Poststenotic Jets in MRI: Dependence on Flow Velocity and on Imaging Parameters," Magnetic Resonance Imaging, vol. 9, pp. 67–72, 1991.

Krug, et al., "MR Imaging of Poststenotic Flow Phenomena: Experimental Studies," JMRI 1991: 1:585–591.

Gatenby, et al., "Mechanisms of Signal Loss in MR Imaging of Stenoses," SMRM 1992, p. 2814.

Frank, et al., "Distortions from Curved Flow in Magnetic Resonance Imaging," 1993, pp. 84–93.

Gatenby, et al., "An Investigation Using Partial Echo Techniques of Post–Stenotic Signal," SMRM 1991, p. 364.

Evans, et al., "Effects of Turbulence on Signal Intensity in Gradient Echo Images," Investigative Radiology, vol. 23, Jul. 1988, pp. 512–518.

P.G. De Gennes, "Theory of Spin Echos in a Turbulent Fluid," Physics Letters, vol. 29A, No. 1, Mar. 1969, pp. 23–24.

Bradley, Jr., et al., "The Appearance of Rapidly Flowing Blood on Magnetic Resonance Images," AJR: 143, Dec. 1964, pp. 1167–1174.

Bradley, et al., "Blood Flow: Magnetic Resonance Imaging," Radiology 1985: 154: 443–450.

Gatenby, et al., "Echo–Planar–Imaging Studies of Turbulent Flow," Journal of Magnetic Resonance, Series A 121, 1996, pp. 193–200.

Li, et al., "Turbulent Pipe Flow studied by Time–Averaged NMR Imaging: Measurements of Velocity Profile and Turbulent Intensity," Magnetic Resonance Imaging, vol. 12, No. 6, pp. 923–934.

Maclin, et al., How to Improve a Neural Network for Early Detection of Hepatic Cancer, Cancer Letters, 77, 1994, pp. 95–101.

Ouyang, et al., "Using a Neural Network to Diagnose the Hypertonic Portions of Hypertonic Cardiomyopathy," M.D. Computing, vol. 15, No. 2, 1998, pp. 106–109.

Adi Armoni, Ph.D., "Use of Neural Networks in Medical Diagnosis," M.D. Computing, vol. 15, No. 2, 1998, pp. 100–104.

Hal S. Stern, Technologies, vol. 38, No. 3, Aug. 1996, pp. 205–213.

Nishimura, et al., "On the Nature and Reduction of the Displacement Artifact in Flow Images," Magnetic Resonance in Medicine, 22, 1991, pp. 481–492.

Garbini, et al., Measurement of Fluid Turbulence Based on Pulsed Ultrasound Techniques, Part 1, Analysis, J. Fluid Mech., vol. 118, 1982, pp. 445–470.

Garbini, et al., "Measurement of Fluid Turbulence Based on Pulsed Ultrasound Techniques, Part 2, Experimental Investigation," J. Fluid Mech. vol. 118, 1982, p. 471–505.

Goodenday, et al., "Identifying Coronary Stenosis Using an Image–Recognition Neural Network," IEEE Engineering in Medicine and Biology, Sep./Oct. 1997, pp. 139–144.

Coppini, et al., "A Neural Network Architecture for Understanding Discrete Three–Dimensional Scenes in Medical Imaging," Computers and Biomedical Research 25, 1992, pp. 569–585.

Fredfelt, et al., "Automatic Screening of Plain Film Mammography," Seminars in Ultrasound, CT, and MRI, vol. 13, No. 2, Apr. 1992, pp. 135–139.

Nekovei, et al., "Back–Propagation Network and its Configuration for Blood Vessel Detection in Angiograms," IEEE Transactions on Neural Networks, vol. 6, No. 1, Jan. 1995, pp. 64–72.

Cios, et al., "Neural Networks in Detection of Coronary Artery Disease," IEEE, 1990, pp. 33–37.

Gao, et al., "Nuclear Magnetic Resonance Signal from Flowing Nuclei in Rapid Imaging Using Gradient Echos," Med. Phys., 15(6), Nov./Dec. 1988, pp. 809–814.

Yuan, et al., "The Solution of Bloch Equations for Flowing Spins During a Selective Pulse Using a Finite Difference Method," Med. Phys, 14(6), Nov./Dec. 1987, pp. 914–921.

Caprihan, et al., "Flow Measurements by NMR," Physics Reports, 198, No. 4, 1990, pp. 195–235.

Doi, et al., "Computer–Aided Diagnosis: Development of Automated Schemes for Quantitative Analysis of Radiographic Images," Seminars in Ultrasound, CT, and MRI, vol. 12, No. 2, Apr. 1992, pp. 140–152.

Duerk, et al., "Experimental Confirmation of Phase Encoding of Instantaneous Derivatives of Position," MRM 32:77–87, 1994.

Dumoulin, et al., "Noninvasive Measurement of Renal Hemodynamic Functions using Gadolinium Enhanced Magnetic Resonance Imaging," MRM 32:370–378, 1994.

Simonetti, et al., "Significance of the Point of Expansion in Interpretation of Gradient Moments and Motion Sensitivity," JMI, vol. 1, No. 5, Sep./Oct. 1991, pp. 569–576.

Schmallbrock, et al., "Volume MR Angiography: Methods to Achieve Very Short Echo Times," Radiology, vol. 175, No. 3, Jun. 1990, pp. 861–865.

Fukuda, et al., "Transition from Laminar to Turbulent Flow of Water in a Pipe Measured by a Pulsed NMR Method," Journal of the Physical Society of Japan, vol. 54, No. 2, Dec. 1985, pp. 4555–4560.

Fukuda, et al., "A Pulsed NMR Study on the Flow of Fluid," Journal of Physical Society of Japan, vol. 47, No. 6, Dec. 1979, pp. 1999–2006.

de Roos et al., Cine MR imaging in aortic stenosis, J Comp Assist Tomogr 13(3): 421–5, 1989 May–Jun.*

Mirowitz et al., Normal signal–void patterns in cardiac cine MR images, Radiology 176(1): 49–55, 1990 Jul.*

* cited by examiner

SYSTEM AND METHOD FOR ANALYZING A MEDICAL IMAGE

CROSS-REFERENCE TO RELATED APPLICATIONS

This application claims priority to copending U.S. provisional patent application entitled "Knowledge Based Medical Image Analysis" filed on Mar. 20, 1998, and accorded serial No. 60/078,811, which is entirely incorporated herein by reference.

STATEMENT REGARDING FEDERALLY SPONSORED RESEARCH AND DEVELOPMENT

The U.S. Government has a paid-up license in this invention and the right in limited circumstances to require the patent owner to license others on reasonable terms as provided for by the terms of Contract No. HL-39437-06A2 awarded by the National Institute of Health.

TECHNICAL FIELD

The present invention is generally related to the field of analysis of a medical image, and, more particularly, is related to a system and method for analyzing a magnetic resonance image of stenosis in blood vessels.

BACKGROUND OF THE INVENTION

Atherosclerosis, the primary cause of heart attack and stroke, is currently responsible for most of the deaths in the Western world. In the United States alone, five million people seek treatment for cardiovascular ailments every year. Several symptoms indicate the need for surgical intervention to alleviate atherosclerotic disease. Some examples of these symptoms are transient ischemic attacks, physical performance on a treadmill stress test, and the existence of a prior incident of artery blockage or narrowing. A particular quantity that has been extensively studied and correlated to the proper clinical treatment is the degree of artery narrowing that is called the "percent stenosis".

Stenoses limit blood flow by raising the resistance to flow through the vessel. For example, the consequence of the stenosis in the cerebral circulation, where there is otherwise little resistance to flow, is that a significant stenosis can reduce the flow to the brain through that artery. In severe stenosis, a negative transmural pressure may be generated via the Bernoulli effect. If this occurs cyclically with the pulse, a stenosis may suddenly fracture because of mechanical fatigue failure which results in free floating particles in the blood flow which may block subsequent lesser blood vessels and result in stroke or other similar occlusive occurrence.

Consistent with hemodynamics studies such as the North American Symptomatic Carotid Endartectomy Trial, clinical observations indicate that patients with stenosis of approximately 60% or greater are candidates for surgery to correct the blockage. Generally, there is significant risk in the surgical methods which is balanced against the risk of having an atherosclerotic event. Accurate quantification of the percent stenosis is therefore critical in maximizing the patient's outcome and in minimizing healthcare costs.

The task of quantifying the severity of atherosclerotic narrowing of blood vessels or percent stenosis is called angiography, which refers to the imaging blood vessels. The current most effective method of angiography employed to determine the percent stenosis is x-ray angiography. In x-ray angiography, a catheter is used to deliver a contrast agent to an upstream location of the stenosis. While the contrast agent is released into the blood flow upstream of the stenosis, x-rays are taken of the stenosis and surrounding area. The contrast agent ensures that the outlines of the blood flow are revealed on the x-ray which indicates any narrowing of the blood vessel in question.

However, x-ray angiography has significant drawbacks. For example, the contrast agent is toxic to the kidneys and some patients can develop an allergic reaction. Also, merely catheterizing a patient may cause a stroke or heart attack. Additionally, complications may arise because the catheter insertion point into the artery can heal slowly which necessitates an overnight stay in the hospital overnight for observation, thereby incurring the associated costs.

Another prospective angiographic method employs magnetic resonance imaging (MRI) technology to generate a view of the region containing stenosis of a blood vessel. However, the images generated using MRI generally suffer from inaccuracies due to the movement of blood through the blood vessel and other reasons. Consequently, the precise percent stenosis is very difficult if not impossible to quantify in a given image and MRI angiography is not practical.

SUMMARY OF THE INVENTION

The present invention provides a system and method for determining a severity of a stenosis in a blood vessel depicted in a magnetic resonance imaging (MRI) data set. Briefly described, in architecture, the system comprises a neural network configured to calculate the severity of the stenosis in the blood vessel based upon a number of input parameters, and the input parameters including at least one characteristic of a signal void associated with the stenosis in the MRI data set.

The present invention can also be viewed as a method for determining a severity of a stenosis in a blood vessel depicted in a magnetic resonance imaging (MRI) data set. In this regard, the method can be broadly summarized by the following steps: identifying a number of input parameters, the input parameters including at least one characteristic of a signal void associated with the stenosis in the MRI data set, and calculating the severity of the stenosis in the blood vessel based upon the input parameters.

The present invention has numerous advantages, one of which is that the present invention allows the easy and cost efficient determination of a percent stenosis in a patient without invasive and high risk surgical procedures. Other advantages of the invention include the fact that it is simple in design, user friendly, robust and reliable in operation, efficient in operation, and easily implemented for mass commercial production.

Other features and advantages of the present invention will become apparent to one with skill in the art upon examination of the following drawings and detailed description. It is intended that all such additional features and advantages be included herein within the scope of the present invention.

BRIEF DESCRIPTION OF THE SEVERAL VIEWS OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE INVENTION

Figure 1A:
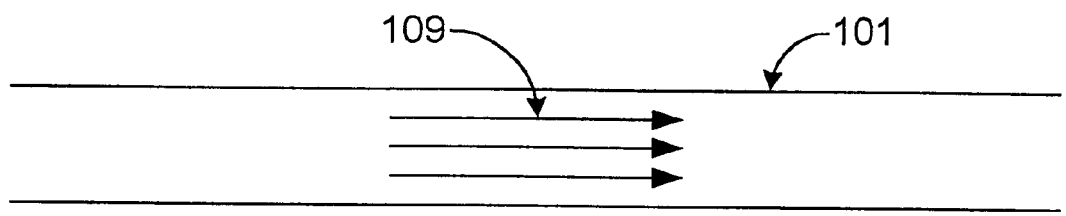
FIG. 1A is an illustration of a normal blood vessel.
Figure 1B:
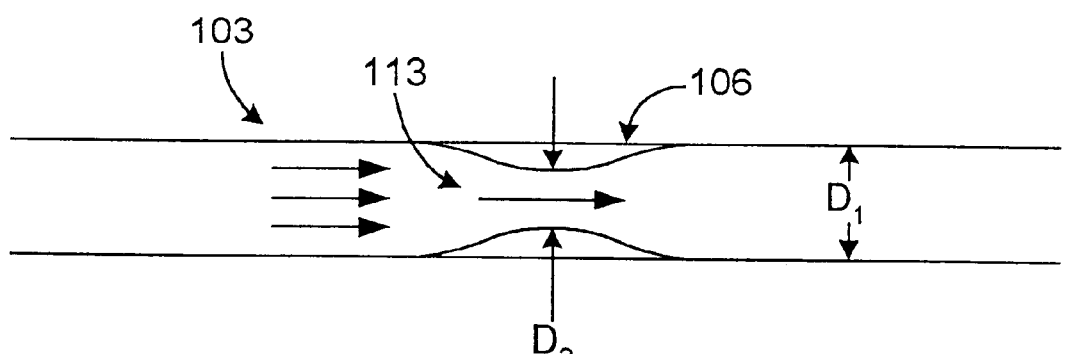
FIG. 1B is an illustration of a blood vessel with stenosis.

Turning to FIGS. 1A and 1B, shown are illustrations of a normal blood vessel 101 and an abnormal blood vessel 109 with stenosis 106. The normal blood vessel 101 has a normal blood flow 103 that is not restricted. The abnormal blood vessel 103 has a constricted blood flow 113 due to the presence of the stenosis 106. Many individuals develop the stenosis 106 resulting in atherosclerosis that may eventually cause death by a heart attack or stroke. The stenosis 106 may occur in any blood vessel in the human body, but is more commonly found in specific locations in particular blood vessels such as those in the heart, brain, legs, and kidneys as known in the medical field.

The severity of the stenosis 106 is characterized by a value known as the percent stenosis. The percent stenosis is determined by identifying a first diameter $D_1$ which is the normal diameter of the blood vessel 103 and a second diameter $D_2$ which is the diameter of the stenosis 106 at its most narrow point. Percent stenosis is calculated according to the following formula:

$$\text{Percent Stenosis} = D_1 - D_2/D_1 \%.$$

Currently, treatment is recommended to relieve the stenosis 106 when the percent stenosis is approximately 60% or greater. See North American Symptomatic Carotid Endarterectomy Trial Collaborators, "Beneficial Effect of Carotid Endarterecomy in Symptomatic Patients with High-Grade Carotid Stenosis. N Engl J Med 325:445–53 (1991), and Downing et al., "Flow Through a Compliant Stenotic Artery," Advances in Bioengineering, American Society of Mechanical Engineers Bioengineering Division, 26:137–140 (1993), the above cited references being incorporated herein by reference.

Figure 2:
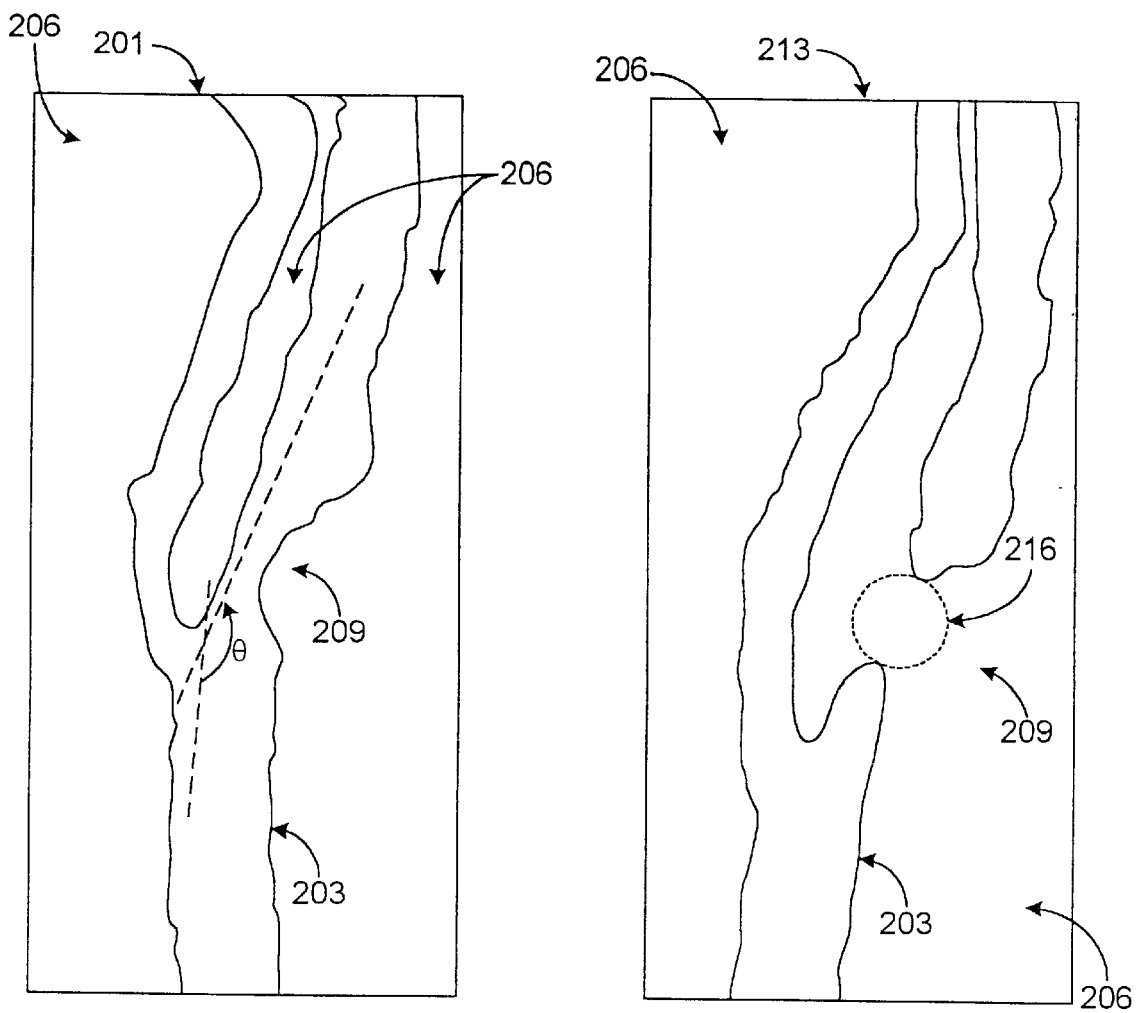
FIG. 2 is a side by side comparison of an x-ray angiogram of a blood vessel with stenosis and a two dimensional image of the same blood vessel generated from a magnetic resonance imaging data set.

With reference to FIG. 2, shown is a side by side comparison of two images which are simplified black and white representations of gray scale images. The first image is an x-ray angiogram 201 of a blood vessel 203 and the surrounding tissue 206. The blood vessel 203 is, for example, the common carotid artery that branches into two lesser arteries, although it is understood that the present invention applies to any blood vessel that may experience stenosis. One of the lesser arteries of the blood vessel 203 is partially blocked by stenosis 209. The second image is a two dimensional representation of a magnetic resonance angiogram 213 ("MRA 213") of the same blood vessel 203 generated from a magnetic resonance imaging data set. The magnetic resonance angiogram 213 is preferably taken at times between heart pulses during times of the least movement of the blood vessel 203 for the best images, although this is not absolutely necessary. See Tsuruda et al., "Artifacts Associated with Magnetic Resonance Neuroangiography", American Journal of Neuroradiology, 13:1411–1422 (1992) which is incorporated herein by reference. Note that the blood vessel has a branch angle θ between the common carotid artery and the lesser artery in which the stenosis 209 occurs. The branch angle θ may be important in analysis that is to be discussed.

Generally, the x-ray angiogram 201 of the blood vessel 203 provides a high degree of accuracy as to the actual extent of the stenosis 209. In particular, the walls of the stenosis 209 are well defined thereby making it possible to easily calculate the percent stenosis. However, the accuracy of the x-ray angiogram 201 is obtained at great risk during an invasive surgical procedure as described in the background above.

In determining the precise dimensions of the stenosis 209, the MRA 213 is problematic. In particular, in the general location of the stenosis 209 there is a signal void 216 which appears as a region with decreased relative image intensity in the gray scale image due to stenosis 209 in the blood vessel 203. The image intensity refers to the intensity of the pixels of the gray scale image. It is quite difficult, if not impossible, to determine the precise percent stenosis due to the signal void 216 as opposed to the x-ray angiogram 201. This is unfortunate because magnetic resonance angiography is a non-surgical, non-invasive procedure with virtually no risk to the patient and is performed at a cost that is far less than x-ray angiography.

Upon further investigation, however, it has been discovered that the signal void 216 may provide information from which the percent stenosis can be determined given other known factors. Thus, further discussion of the nature of the signal void 216 is deemed appropriate.

It has been determined that the signal void 216 occurs due to the inability of a magnetic resonance imaging device to accurately obtain information from random movement in the blood stream. Specifically, magnetic resonance imaging employs magnetic and electromagnetic fields to manipulate the protons of the particular subject under scrutiny in "slices". Based on the frequency of the electromagnetic fields applied, the protons in a particular slice emit a signal, which is acquired. The frequency of the excitation signal is proportional to the magnetic field strength. The magnetic field strength is altered such that the frequency varies with position in the slice. The protons emit a signal at the excitation frequency received. Consequently, the location of the protons along one dimension in a particular slice is determined by the frequency of the signal they emit. Their location in a second dimension is determined by phase shifts. A Fourier transform is performed on the information obtained and the subject is reconstructed into an image as is known in the art.

The protons present in the blood that courses through the stenosis 209 of the blood vessel 203 experience acceleration in the middle of the stenosis 209 and a degree of turbulence after the stenosis 209, the degree of turbulence varying depending upon the percent stenosis and the actual physical dimensions of the stenosis 209. The signal void 216 is created by various mechanisms related to the acceleration and turbulence. One of these mechanisms is intravoxel phase dispersion related to the acceleration and turbulence that causes random motion of the protons present in the blood. This randomization results in intravoxel phase dispersion with different phase shifts being obtained in a voxel, resulting in destructive interference that appears as the signal void 216 in the final image.

A second mechanism resulting in the signal void 216 is phase misregistration artifact, sometimes referred to as "ghosting" in the literature, which refers to the fact that the location of the protons present in the blood do not stay stationary due to the randomization. Consequently, from slice to slice variations in the flow field appear to be at different spatial frequencies. Note that phase misregistration artifact is not specific to the signal void 216 alone, but may appear in other locations outside the signal void 216 as well.

Thus, it has been found there is a correlation between turbulence, or random movement, of water molecules in blood and the nature and extent of the signal void 216. Consequently, the size and nature of the signal void 216 provides information as to the anatomy or, particularly, the stenosis 209 which created it. Therefore, the signal void 216 can be seen as a signature of the stenosis 209.

Figure 3:
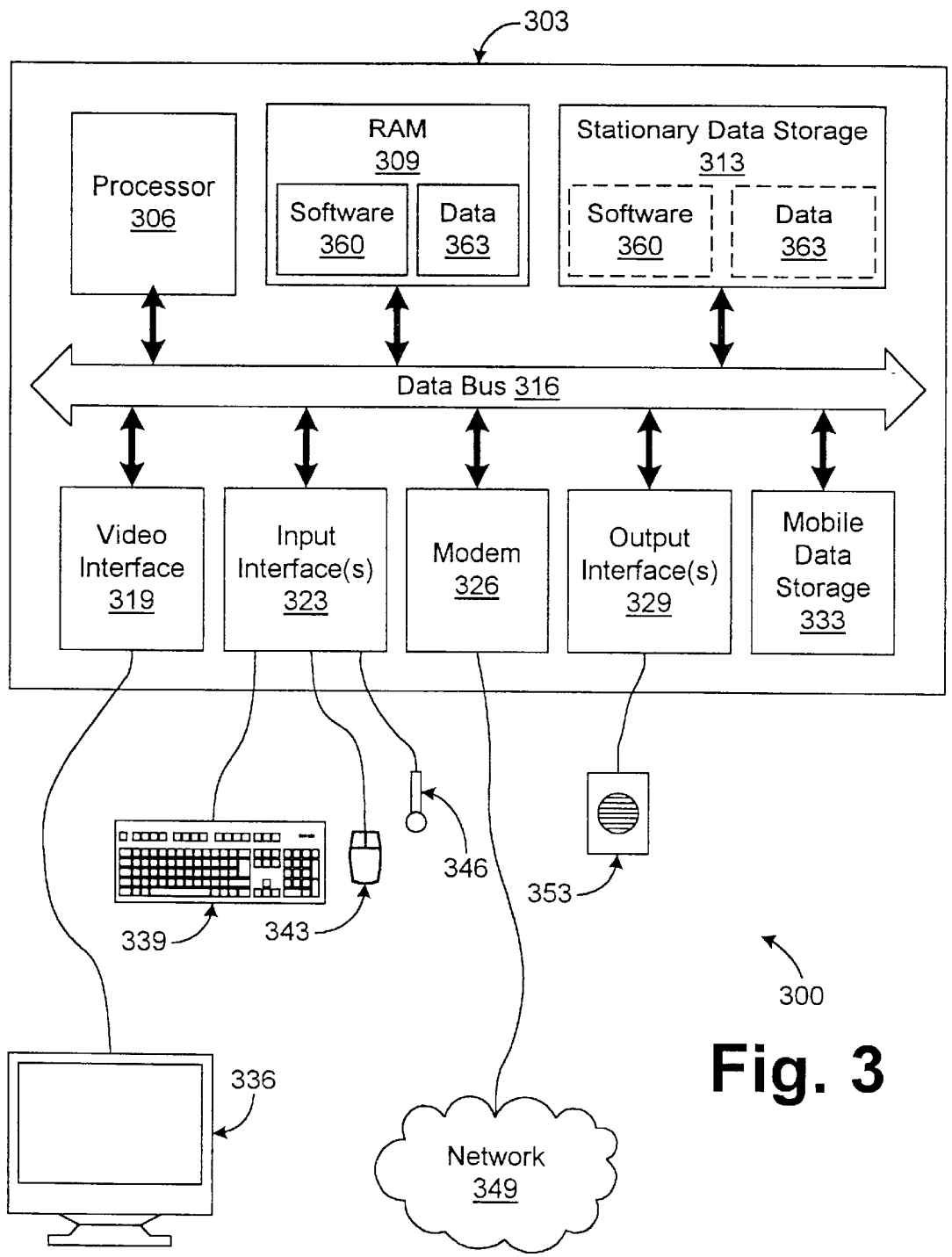
FIG. 3 is a block diagram of a system according to the present invention.

Referring to FIG. 3, shown is a block diagram of a medical image analysis system 300 according to an embodiment of the present invention. The medical image analysis system 300 includes a computer system 303 which comprises a processor 306, a random access memory (RAM) 309, and a stationary data storage device 313, all of which are coupled to a data bus 316. The computer system 303 further comprises a video interface 319, a number of input interfaces 323, a modem 326, a number of output interfaces 329, and a mobile data storage device 333, all of which are also coupled to the data bus 316. The stationary data storage device 313 may include, for example, a hard drive, compact disk read only memory, or other similar device.

The medical image analysis system 300 also includes a display device 336 that is coupled to the data bus 316 via the video interface 319. The display device 336 may be a cathode-ray tube, liquid crystal display screen, or like device. The medical image analysis system 300 also includes several input devices, namely, a keyboard 339, a mouse 343, and a microphone 346 which are all coupled to the data bus 316 via the various input interfaces 323. In addition, the modem 326 is coupled to an external network 349 thus allowing the computer system to send and receive data via the external network 349. The external network 349 may be, for example, the Internet or other similar network.

The medical image analysis system 300 may further include audio speakers 353 or other output devices that are coupled to the data bus 316 via the output interfaces 329. The mobile data storage device 333 may be one of several such devices that allow storage of data on a mobile platform such as a floppy disk drive, compact disc drive, mobile hard drive, or other similar data storage device.

The medical image analysis system 300 also includes image analysis software 360 which are generally stored on the stationary data storage device 313 along with data 363. When the medical image analysis system 300 is operational, pertinent portions of the image analysis software 360 are loaded into the RAM 309 and is executed by the processor 306. During operation of the medical image analysis system 300, the image analysis software 360 may access the data 363 stored on the stationary data storage device 313, loading the data 363 into the RAM 309 for various purposes as will be discussed.

Figure 4:
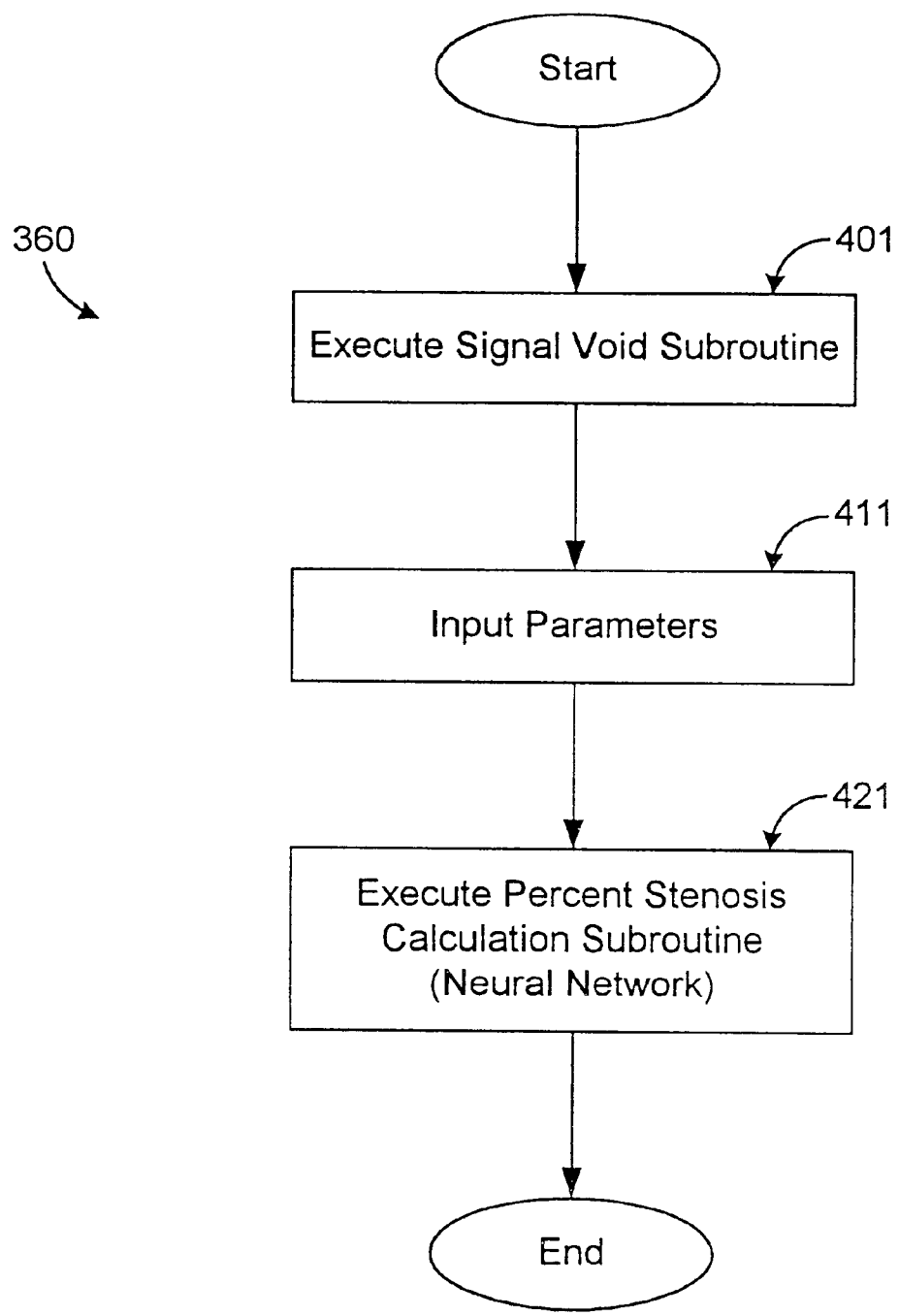
FIG. 4 is a flow chart of the image analysis software stored in memory and executed by the system of FIG. 3.

With reference to FIG. 4, shown is a flow chart of the image analysis software 360. The image analysis software 360 begins with block 401 in which a signal void subroutine is executed. In the signal void subroutine 401, a two dimensional magnetic resonance angiogram (MRA) 213 (FIG. 2) is generated of a blood vessel using magnetic resonance imaging data from a patient, and pertinent characteristics of the signal void 316 (FIG. 3) and other image characteristics appearing in the image are determined therefrom. The MRA 213 is generated from a magnetic resonance image data set which is part of the data 363 (hereafter "MRI data 363") that is stored on either the stationary data storage 313 (FIG. 3), or on a portable platform such as a floppy disk, compact disk, or other like medium that is placed in the mobile data storage device 333 (FIG. 3). Ultimately, the MRI data 363 set is loaded from one of these storage places into the RAM 309 (FIG. 3) and manipulated by the processor in generating the MRA 213.

Note that the MRI data 363 may also be transmitted to the image analysis system 300 (FIG. 3) via the network 349 (FIG. 3) and the modem 326 (FIG. 1). This allows MRI data to be transmitted to the image analysis system 300 from almost any location where the patients are examined. Such MRI data is downloaded from the network 349 and stored on the stationary data storage device 313, etc.

Next, in block 411, additional parameters such as anatomic or other parameters associated with the particular patient are input into the image analysis system 300. Such parameters may include, but are not limited to, the blood flow rate, the presence of recirculation flow streak, and the branch angle θ if there is a relevant bend in the blood vessel 203 (FIG. 2). Note that the rate of blood flow through the vessel is preferably determined between heart pulses when blood flow is generally more constant, a period commonly referred to as diastole as discussed by Saloner et al., "MRA Studies of Arterial Stenosis: Improvements by Diastolic Acquisition", Magnetic Resonance in Medicine, vol. 31, no. 2, pp. 196–203, which is incorporated herein by reference. The actual rate of blood flow through the blood vessel in question may be determined using a technique called phase velocity mapping in which the flow rate of the blood is measured in a plane perpendicular to the blood vessel axis well distal to the signal void 216. A discussion of phase velocity mapping may be found in Firmin et al., "The Application of Phase Shifts in NMR for Flow Measurement", Magnetic Resonance in Medicine, 14:230–241 (1990a), which is incorporated herein by reference. Finally, in block 421, a percent stenosis calculation subroutine is executed in which the percent stenosis is calculated based upon the signal void characteristics and the physiology parameters, preferably using a neural network.

Figure 5:
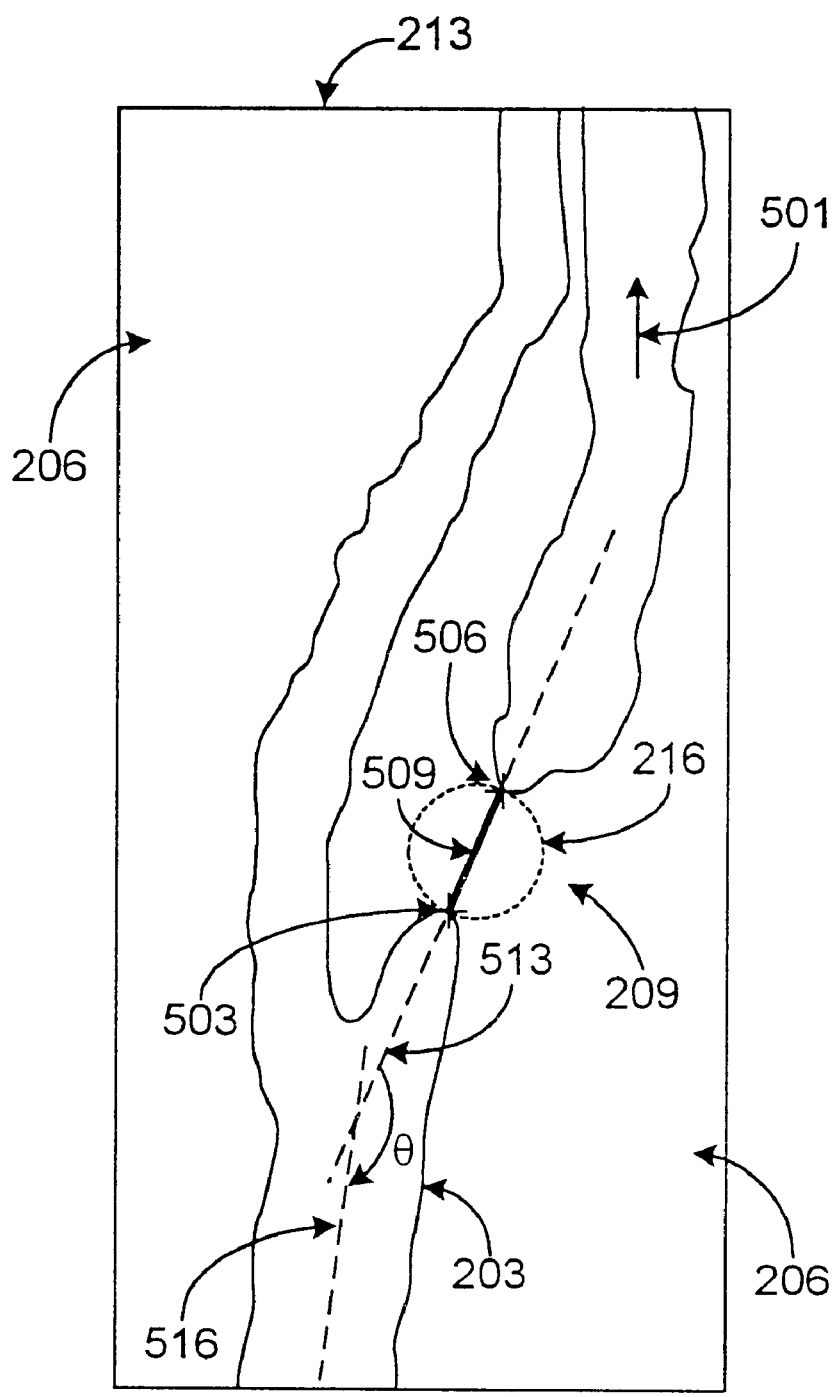
FIG. 5 is a magnetic resonance imaging angiogram generated by the image analysis software of FIG. 4.

With reference to FIG. 5, shown is the two dimensional MRA 213 which serves as an example of those that are generated in block 401 (FIG. 4). The direction of the blood flow 501 is as indicated. Both a proximal end 503 and a distal end 506 of the signal void 216 are indicated with a longitudinal axis 509 formed therebetween. A first vessel axis 513 and a second vessel axis 516 run along the direction of the main portion and the branch portion of the blood vessel 203, forming the branch angle θ therebetween. From the MRA 213, various signal void characteristics can be determined. For example, the length of the longitudinal axis 509 and the intensity along the longitudinal axis 509 may be determined. In particular, the intensity provides useful information as to the extent of the underlying turbulence in the blood. In addition, the second moment of intensity along the longitudinal axis 509 with respect to the distal end is important as it provides the standard deviation of the turbulence.

Figure 6:
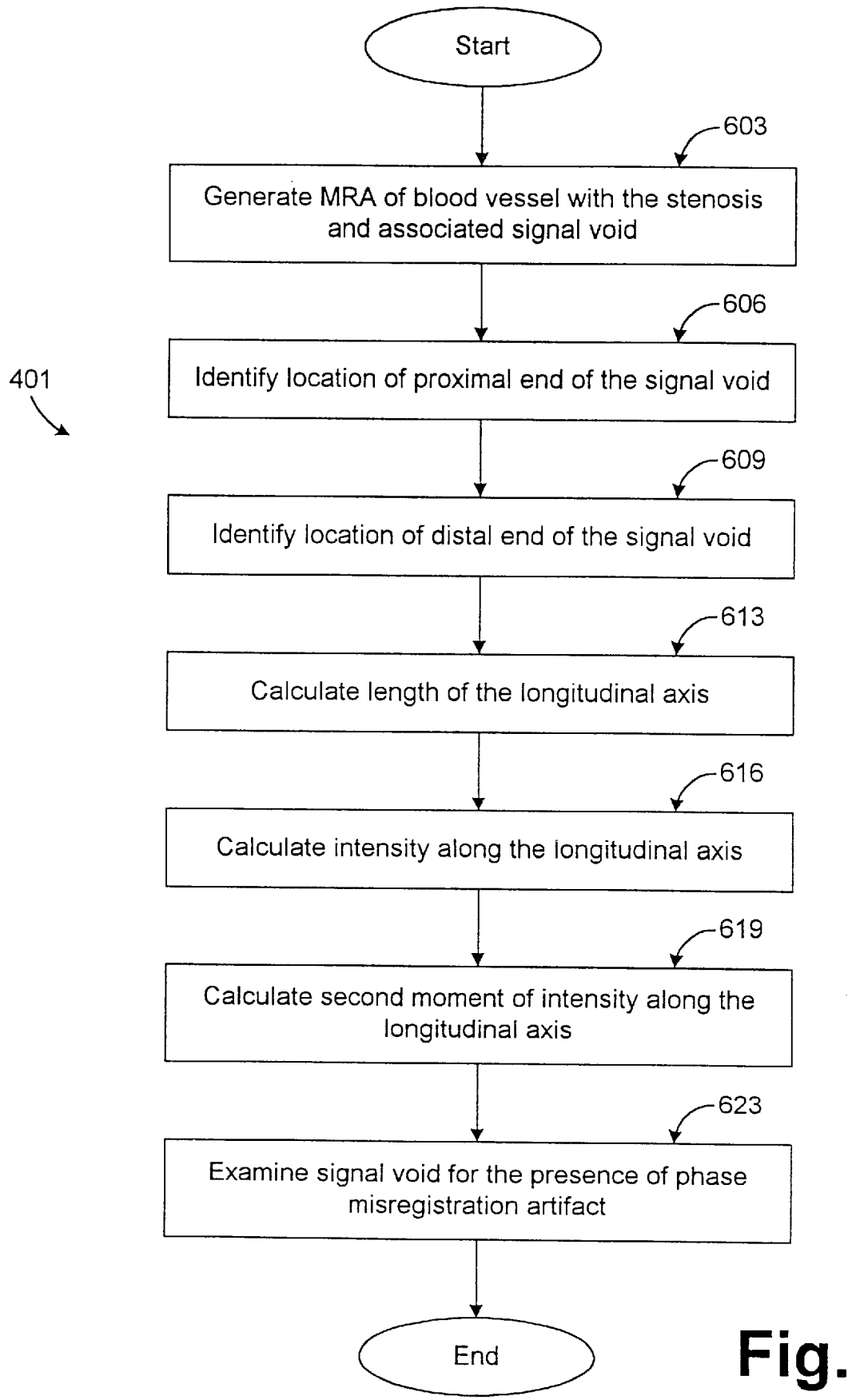
FIG. 6 is a flow chart of a subroutine of the image analysis software of FIG. 4.

Turning then, to FIG. 6, shown is a flow chart of the signal void subroutine 401 in which the pertinent anatomic characteristics and image characteristics of the MRA 213 are determined. Beginning with block 603, the MRA 213 (FIG. 5) of the blood vessel 203 (FIG. 5) with stenosis 209 (FIG. 5) is generated on the display device 336 (FIG. 3) from MRI data 363 (FIG. 3) which is preferably three dimensional data of the slices obtained from the patient. Specific software used to generate the MRA 213 may employ "maximum intensity projection" or other equivalent techniques as known by those skilled in the art and, consequently, is not discussed in detail herein. In cases where the blood vessel is straight, one may simply pick a single dimensional slice from the MRI data 363 from an oblique plane through the target blood vessel to use as the MRA 213. Next, in block 606, the proximal end 503 of the signal void 216 (FIG. 5) is located and, in block 609, the distal end 506 of the signal void 216 is located. Note that locating the proximal and distal ends 503 and 506 may be accomplished, for example, by manipulating the mouse 343 (FIG. 3) so as to locate a point or cross on each location, where depressing a button of the mouse confirms the location. Thereafter, in block 613, the length of the longitudinal axis 509 (FIG. 5) formed between the proximal and distal ends 503 and 506 is plotted and the length of the longitudinal axis 509 is calculated. The length of the signal void 216 is an important signal void characteristic obtained from the MRA 213.

Moving to block 616, another signal void characteristic comprising the intensity of the signal void 216 along the longitudinal axis 509 is calculated. Thereafter, in block 619, an addition signal void characteristic comprising the second moment or standard deviation of the intensity along the longitudinal axis 509 is calculated. The signal void subroutine 401 then examines the MRA 213 for an image characteristic comprising the presence of phase misregistration artifact in block 623. The presence of phase misregistration artifact is noted with a logical zero for "no" and a logical one for "yes". Thereafter, the signal void subroutine 401 ends and the image analysis software 300 (FIG. 4) reverts to block 411 (FIG. 4).

Figure 7:
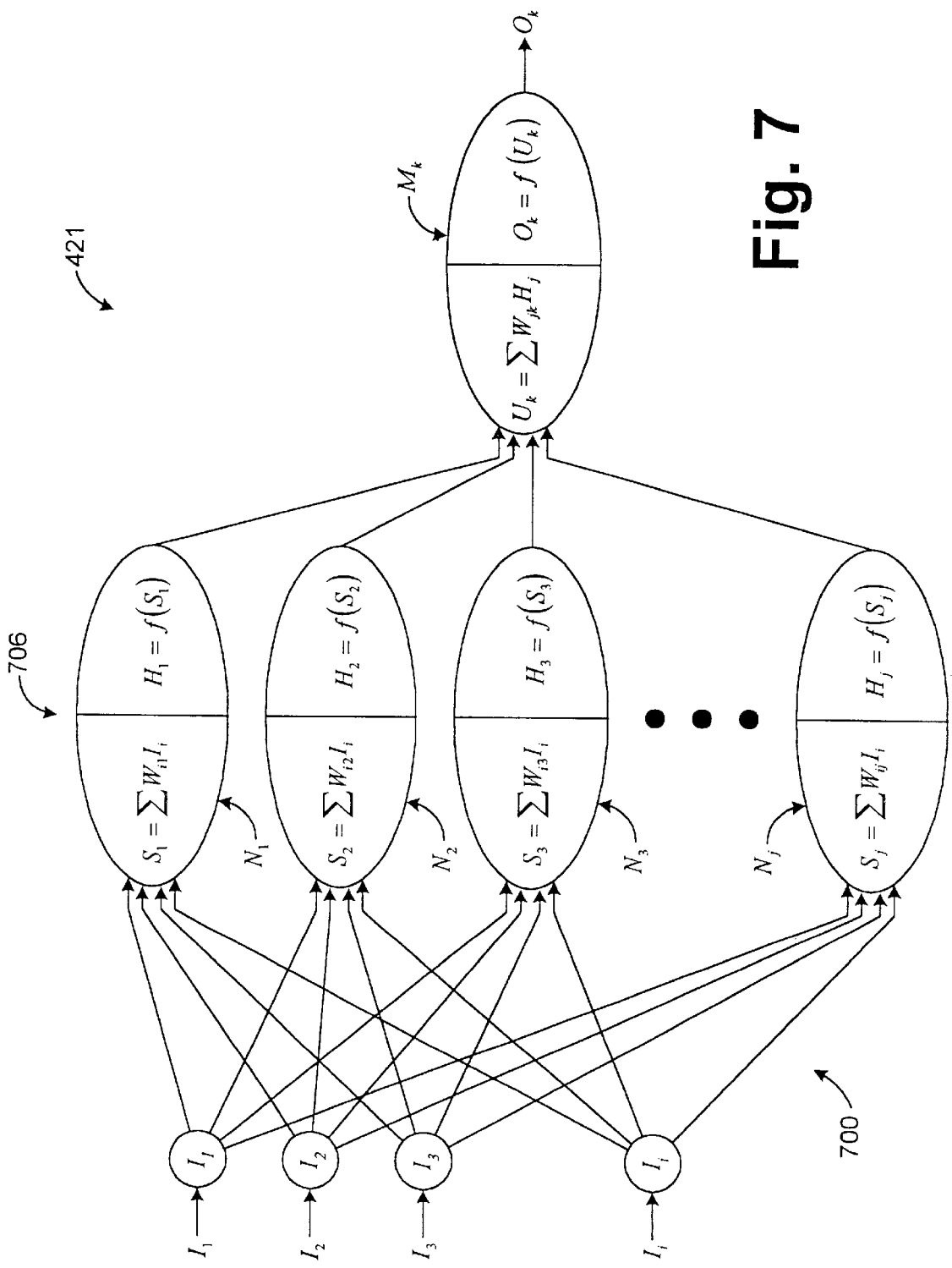
FIG. 7 is a block diagram of a neural network executed in a subroutine of the image analysis software of FIG. 4.

With reference to FIG. 7, shown is a functional block diagram of the percent stenosis calculation subroutine 421. The percent stenosis calculation subroutine 421 preferably employs a neural network 700 which includes multiple inputs $I_i$ that are applied to generate one or more outputs $O_k$. The neural network 700 includes several input nodes 703 to which the inputs $I_i$ are applied. The inputs $I_i$ are the signal void characteristics, image characteristics, and the anatomic parameters discussed previously. In the preferred embodiment, the specific signal void characteristics, image characteristics, and anatomic parameters applied as inputs $I_i$ to the neural network 700 include the length of the longitudinal axis of the signal void 216 (FIG. 2), the average image intensity along the longitudinal axis 509 (FIG. 5), the second moment of image intensity along the longitudinal axis, the presence of phase misregistration artifact (0="no", 1="yes"), blood flow rate, presence of recirculation flow streak (0="no", 1="yes"), and the branch angle. Note however, the present invention is not limited to these inputs as other signal void characteristics, image characteristics, or anatomic parameters may be employed as well as discussed below.

The output $O_k$ of the neural network 700 is preferably the percent stenosis in the blood vessel 203 (FIG. 5). However, other outputs may be included such as a certainty value which, for example, may range from 0 to 1 thereby indicating the level of certainty that the percent stenosis is correct.

The neural network 700 also includes a hidden layer 706 that comprises multiple neurons $N_j$. It is understood that while only a single hidden layer 706 is shown, that there may be multiple hidden layers 706, each with a predetermined number of neurons $N_j$. In a particular embodiment for example, a single hidden layer 706 was used with a total of four neurons employed with significant success and accuracy in determining the percent stenosis. The neural network 700 also includes at least one output node $M_k$ that generates the output $O_k$. It is understood that there may be more than a single output node $M_k$ if so desired.

In calculating an output $O_k$, the inputs $I_i$ are applied to the input nodes 703 which thereafter supply a copy of the inputs $I_i$ to each of the neurons $N_j$ in the hidden layer 706. Generally, the neurons $N_j$ that are simplified versions of biological neurons, are capable of performing a simple mathematical task. The output of each neuron $N_j$ is a nonlinear function of its inputs. Upon receiving the inputs $I_i$, the neurons $N_j$ perform a summation $S_j$ of a weighted multiplication of each input $I_i$ defined by $$S_j = \Sigma W_{ij} I_i$$

where $W_{ij}$ is defined as the weighting factor associated with each respective input $I_i$. If the summation $S_j$ reaches a saturation value of the neuron $N_j$, then the neuron $N_j$ this "activated" and outputs a non-zero value. The neural output $H_j$ is calculated using the neuron activation function f(x) which may be, for example, a hyperbolic tangent sigmoidal function or a linear ramp function. These neuron activation functions differ somewhat from the function of a biological neuron, which has an activation function that more closely resembles a step function. The neural output $H_j$ of each neuron $N_j$ is calculated by $$H_j = f(S_j).$$

The outputs $H_j$ are then applied to an output node $M_k$ that performs a summation $U_k$ of a weighted multiplication of each neural output $H_j$ defined by $$U_k = \Sigma W_{jk} H_j$$

where $W_{jk}$ is the weighting factor associated with each respective neural output $H_j$. Finally, the output $O_k$ is calculated as using the output node activation function f as function of the summation $U_k$, where $$O_k = f(U_k).$$

The neural network 700 is a "feedforward" neural network in that each neuron $N_i$ processes all of the inputs from a previous layer by accepting a weighted sum of these inputs. It is understood that other types of neural networks such as feedback neural networks may be employed as well, where the input of a neuron $N_i$ is also one of that neuron's outputs.

Before the neural network 700 can be used to generate the output(s) $O_k$ from the inputs $I_i$, the neural network 700 is trained to recognize patterns using supervised training methods known to those skilled in the art. Training is accomplished first by identifying a number of sets of training inputs $I_i$, or training input sets, each training input set having a corresponding desired output(s). During training, the neural network 700 is exposed to the training input sets, thereby generating a corresponding output(s). The corresponding output(s) $O_k$ from the output node $M_k$ is compared to the desired output(s) from each training input set. A mean-squared network error is then calculated between the corresponding and desired output(s) and thereafter, the neural network 700 adjusts its weighting factors W to minimize this error. The application of all of the training input sets to be used in a given circumstance is called an epoch. Generally, several epochs occur before the neural network 700 is trained acceptably. This process is repeated with sets of known input(s)/outputs(s) until the mean-squared error of the output(s) is below a prescribed tolerance.

There are several techniques used to train a neural network 700 as known by those skilled in the art. The above discussion contemplates that any such method may be employed. Perhaps the most common method is termed backpropagation which is known in the art. Note also that the number of hidden layers 706 and the number of output nodes $M_k$ may vary depending upon the number of training input sets that are available to train the neural network 700. Generally, a more complex network should be trained with more training sets to provide accurate output values.

Note, other approaches that may be used to calculate the percent stenosis based on the various inputs discussed herein include other statistical methods which can be used to model the relationship between the various input parameters and the percent stenosis. These approaches may include, for example, traditional multivariate nonlinear regression, principal component analysis, and discriminant analysis. Due to the difficulty identifying needed assumptions about curve fitting for nonlinear regression and, generally, due to the nonlinear relationships between the input parameters and the percent stenosis, these alternative approaches may not perform as accurately as the neural network 700, but may ultimately suffice.

The signal void characteristics and the anatomic parameters applied as inputs $I_i$ to the neural network 700 may also include characteristics and parameters not discussed above. For example, additional anatomic parameters might include a curvature of the blood vessel and the diameter of the blood vessel in addition to other parameters. Note that a crude measurement of the curvature of a blood vessel may be obtained in a manner similar to that in which the branch angle θ is determined as discussed previously, although other methods may be employed as well. Also, for different blood vessels, different combinations of various signal void characteristics and anatomic parameters may be employed to obtain accurate output values.

In addition, the image analysis software 360 (FIG. 3) of the present invention can be implemented in hardware, software, firmware, or a combination thereof. In the preferred embodiment(s), the image analysis software 360 is implemented in software or firmware that is stored in a memory and that is executed by a suitable instruction execution system.

The flow charts and functional block diagrams of FIGS. 4–7 shows the architecture, functionality, and operation of a possible implementation of the image analysis software 360. In this regard, each block represents a module, segment, or portion of code, which comprises one or more executable instructions for implementing the specified logical function(s). It should also be noted that in some alternative implementations, the functions noted in the blocks may occur out of the order noted in FIGS. 4, 6, and 7. For example, two blocks shown in succession in FIG. 4 may in fact be executed substantially concurrently or the blocks may sometimes be executed in the reverse order, depending upon the functionality involved, as will be further clarified hereinbelow.

The image analysis software 360, which comprises an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Other references which are deemed important to the present invention include: Perman et al., "Artifacts from Polsatile Flow in Magnetic Resonance Imaging", Journal of Computer Assisted Tomography, 10: 473–483 (1986); Siegel et al., "Computational Simulation of Turbulent Signal Loss in 2D Time-of-Flight Magnetic Resonance Angiograms", Magnetic Resonance in Medicine, 37: 609–614 (1997); Seigel et al., "Comparison of Phantom and Computer-Simulated Images of Flow in a Convergent Geometry: Implications for Improved Two Dimensional Magnetic Resonance Angiography", Journal of Magnetic Resonance Imaging, 5:677–683 (1995; Bradley et al., "The Appearance of Rapidly Flowing Blood on Magnetic Resonance Images", AJR, 143:1157–1174 (1984); Firmin et al., "The Application of Phase Shifts in NMR for Flow Measurement", Magnetic Resonance in Medicine, 14:230–241 (1990a); Armoni, A., "Use of Neural Networks in Medical Diagnosis", M. D. Computing, 15:100–104 (1998); Jain et al., "On Training Sample Size and Complexity of Artificial Neural Net Classifier", Informatica, vol. 3, no. 3, pp. 301–337 (1992); and Scarselli et al., "Universal Approximation Using Feedforward Neural Networks: A Survey of Some Existing Methods, and Some New Results", Neural Networks, vol. 11, no. 1, pp. 15–37, (1998), all of the above listed references being incorporated herein by reference.

Many variations and modifications may be made to the above-described embodiment(s) of the invention without departing substantially from the spirit and principles of the invention. All such modifications and variations are intended to be included herein within the scope of the present invention.

Therefore, having thus described the invention, the following is claimed:

1. A system for determining a severity of a stenosis in a blood vessel depicted in a magnetic resonance imaging (MRI) data set, comprising:

a neural network configured to calculate the severity of the stenosis in the blood vessel based upon a number of input parameters;

the input parameters including at least one characteristic of a signal void associated with the stenosis in the MRI data set; and a signal void analyzer configured to identify the characteristic of the signal void in the MRI set, wherein the signal void analyzer includes a graphical display generator configured to generate a two dimensional image of the signal void from the MRI data set, and a graphical plotter configured to plot at least two points on the two dimensional image and to determine the length of a line between the two points.

2. The system of claim 1, wherein the signal void analyzer further comprises:

an average image intensity calculator configured to determine an average image intensity along the line; and a second moment calculator configured to determine a second moment of image intensity along the line.

3. The system of claim 1, wherein the neural network is configured to calculate the severity of the stenosis based upon a flow rate of blood through the blood vessel.

4. The system of claim 1, wherein the neural network is configured to calculate the severity of the stenosis based upon a length of a longitudinal axis of the signal void, an average image intensity along the longitudinal axis of the signal void, and a presence of phase misregistration artifact.

5. The system of claim 4, wherein the phase misregistration artifact includes a first component from inside the signal void and a second component from outside the signal void.

6. The system of claim 1, wherein the neural network is configured to calculate the severity of the stenosis based upon a length of a longitudinal axis of the signal void.

7. The system of claim 6, wherein the neural network is configured to calculate the severity of the stenosis based upon an average image intensity along the longitudinal axis of the signal void.

8. The system of claim 6, wherein the neural network is configured to calculate the severity of the stenosis based upon a second moment of image intensity along the longitudinal axis of the signal void.

9. The system of claim 1, wherein the neural network is configured to calculate the severity of the stenosis based upon a presence of phase misregistration artifact.

10. The system of claim 1, wherein the neural network is configured to calculate the severity of the stenosis based upon a presence of recirculation flow streak.

11. The system of claim 1, wherein the neural network is configured to calculate the severity of the stenosis based upon a branch angle of the blood vessel.

12. The system of claim 1, wherein the neural network is configured to calculate the severity of the stenosis based upon intravoxel phase dispersion.

13. The system of claim 1, wherein the neural network is configured to calculate the severity of the stenosis based upon a diameter of the blood vessel.

14. The system of claim 1, wherein the neural network is configured to calculate the severity of the stenosis based upon a curvature of the blood vessel.

15. The system of claim 1, wherein the neural network is configured to calculate the severity of the stenosis based upon an axis of the blood vessel.

16. The system of claim 1, wherein the neural network is configured to calculate the severity of the stenosis based upon a direction of blood flow.

17. The system of claim 1, wherein the neural network is configured to calculate the severity of the stenosis based upon a standard deviation of the turbulence.

18. The system of claim 1, wherein the neural network is feedforward.

19. The system of claim 1, wherein the neural network is feedback.

20. A system for determining a severity of a stenosis in a blood vessel depicted in a magnetic resonance imaging (MRI) data set, comprising:

means for calculating the severity of the stenosis in the blood vessel based upon a number of input parameters;

the input parameters including at least one characteristic of a signal void associated with the stenosis in the MRI data set; and an analyzer means for identifying a number of predetermined characteristics of the signal void in the MRI data set, wherein the analyzer means includes means for generating a two dimensional image of the signal void from the MRI data set, and means for plotting at least two points on the two dimensional image and to determine the length of a line between the two points.

21. The system of claim 20, wherein the analyzer means further comprises:

means for determining an average image intensity along the line; and means for determining a second moment of image intensity along the line.

22. The system of claim 20, wherein the means for calculating the severity of the stenosis includes a means for calculating the severity of the stenosis based upon a flow rate of blood through the blood vessel.

23. The system of claim 20, wherein the means for calculating the severity of the stenosis includes a means for calculating the severity of the stenosis based upon a length of a longitudinal axis of the signal void, an average image intensity along the longitudinal axis of the signal void, and a presence of phase misregistration artifact.

24. The system of claim 20, wherein the phase misregistration artifact includes a first component from inside the signal void and a second component from outside the signal void.

25. The system of claim 20, wherein the means for calculating the severity of the stenosis includes a means for calculating the severity of the stenosis based a presence of phase misregistration artifact.

26. The system of claim 20, wherein the means for calculating the severity of the stenosis includes a means for calculating the severity of the stenosis based a presence of recirculation flow streak.

27. The system of claim 20, wherein the means for calculating the severity of the stenosis includes a means for calculating the severity of the stenosis based upon a branch angle of the blood vessel.

28. The system of claim 20, wherein the means for calculating the severity of the stenosis includes a means for calculating the severity of the stenosis based upon intravoxel phase dispersion.

29. The system of claim 20, wherein the means for calculating the severity of the stenosis includes a means for calculating the severity of the stenosis based upon a diameter of the blood vessel.

30. The system of claim 20, wherein the means for calculating the severity of the stenosis includes a means for calculating the severity of the stenosis based upon a curvature of the blood vessel.

31. The system of claim 20, wherein the means for calculating the severity of the stenosis includes a means for calculating the severity of the stenosis based upon an axis of the blood vessel.

32. The system of claim 20, wherein the means for calculating the severity of the stenosis includes a means for calculating the severity of the stenosis based upon a direction of blood flow.

33. The system of claim 20, wherein the means for calculating the severity of the stenosis includes a means for calculating the severity of the stenosis based upon a standard deviation of the turbulence.

34. The system of claim 20, wherein the neural network is feedforward.

35. The system of claim 20, wherein the neural network is feedback.

36. A method for determining a severity of a stenosis in a blood vessel depicted in a magnetic resonance imaging (MRI) data set, comprising the steps of:

identifying a number of input parameters, the input parameters including at least one characteristic of a signal void associated with the stenosis in the MRI data set, wherein the step of identifying the number of input parameters includes the step of determining a length of a longitudinal axis of the signal void, an average image intensity along the longitudinal axis of the signal void, and a presence of phase misregistration artifact; and calculating the severity of the stenosis in the blood vessel based upon the input parameters.

37. The method of claim 36, wherein the step of identifying the number of parameters further includes the step of determining an intravoxel phase dispersion.

38. The method of claim 36, wherein the step of identifying the number of parameters further includes the step of determining a diameter of the blood vessel.

39. The method of claim 36, wherein the step of identifying the number of parameters further includes the step of determining a curvature of the blood vessel.

40. The method of claim 36, wherein the step of identifying the number of parameters further includes the step of determining a axis of the blood vessel.

41. The method of claim 36, wherein the step of identifying the number of parameters further includes the step of determining a direction of blood flow.

42. The method of claim 36, wherein the step of identifying the number of parameters further includes the step of determining a standard deviation of the turbulence.

43. The method of claim 36, wherein the step of calculating the severity of the stenosis is accomplished with a feedforward neural network.

44. The method of claim 36, wherein the step of calculating the severity of the stenosis is accomplished with a feedback neural network.

45. The method of claim 36, wherein the step of identifying the number of parameters further includes the step of determining a second moment of intensity along the longitudinal axis of the signal void.

46. The method of claim 36, wherein the step of calculating the severity of the stenosis is accomplished with a traditional multivariate nonlinear regression.

47. The method of claim 36, wherein the step of calculating the severity of the stenosis is accomplished with a principal component analysis.

48. The method of claim 36, wherein the step of calculating the severity of the stenosis is accomplished with a discriminant analysis.

49. The method of claim 36, wherein the phase misregistration artifact includes a first component from inside the signal void and a second component from outside the signal void.

50. A method for determining a severity of a stenosis in a blood vessel depicted in a magnetic resonance imaging (MRI) data set, comprising the steps of:

identifying a number of input parameters, the input parameters including at least one characteristic of a signal void associated with the stenosis in the MRI data set, wherein the step of identifying the number of input parameters further includes the step of determining a length of a longitudinal axis of the signal void and the step of determining a flow rate of blood through the blood vessel; and calculating the severity of the stenosis in the blood vessel based upon the input parameters.

51. The method of claim 50, wherein the step of identifying the number of parameters further includes the step of determining an intravoxel phase dispersion.

52. The method of claim 50, wherein the step of identifying the number of parameters further includes the step of determining a diameter of the blood vessel.

53. The method of claim 50, wherein the step of identifying the number of parameters further includes the step of determining a curvature of the blood vessel.

54. The method of claim 50, wherein the step of identifying the number of parameters further includes the step of determining a axis of the blood vessel.

55. The method of claim 50, wherein the step of identifying the number of parameters further includes the step of determining a direction of blood flow.

56. The method of claim 50, wherein the step of identifying the number of parameters further includes the step of determining a standard deviation of the turbulence.

57. The method of claim 50, wherein the step of calculating the severity of the stenosis is accomplished with a feedforward neural network.

58. The method of claim 50, wherein the step of calculating the severity of the stenosis is accomplished with a feedback neural network.

59. The method of claim 50, wherein the step of identifying the number of parameters further includes the step of determining a second moment of intensity along the longitudinal axis of the signal void.

60. The method of claim 50, wherein the step of calculating the severity of the stenosis is accomplished with a traditional multivariate nonlinear regression.

61. The method of claim 50, wherein the step of calculating the severity of the stenosis is accomplished with a principal component analysis.

62. The method of claim 50, wherein the step of calculating the severity of the stenosis is accomplished with a discriminant analysis.

63. A method for determining a severity of a stenosis in a blood vessel depicted in a magnetic resonance imaging (MRI) data set, comprising the steps of:

identifying a number of input parameters, the input parameters including at least one characteristic of a signal void associated with the stenosis in the MRI data set, and wherein the step of identifying the number of input parameters further includes the step of determining an average image intensity along the longitudinal axis and the step of determining a flow rate of blood through the blood vessel; and calculating the severity of the stenosis in the blood vessel based upon the input parameters.

64. A method for determining a severity of a stenosis in a blood vessel depicted in a magnetic resonance imaging (MRI) data set, comprising the steps of:

identifying a number of input parameters, the input parameters including at least one characteristic of a signal void associated with the stenosis in the MRI data set, wherein the step of identifying the number of input parameters includes the steps of, generating a two dimensional image of the signal void from the MRI data set, and plotting at least two points on the two dimensional image and to determine the length of a line between the two points; and calculating the severity of the stenosis in the blood vessel based upon the input parameters.

65. The method of claim 64, wherein the step of identifying the predetermined characteristics of the signal void further comprises the steps of:

determining an average image intensity along the line; and determining a second moment of image intensity along the line.

66. The method of claim 64, wherein the step of identifying the number of parameters further includes the step of determining an intravoxel phase dispersion.

67. The method of claim 64, wherein the step of identifying the number of parameters further includes the step of determining a diameter of the blood vessel.

68. The method of claim 64, wherein the step of identifying the number of parameters further includes the step of determining a curvature of the blood vessel.

69. The method of claim 64, wherein the step of identifying the number of parameters further includes the step of determining a axis of the blood vessel.

70. The method of claim 64, wherein the step of identifying the number of parameters further includes the step of determining a direction of blood flow.

71. The method of claim 64, wherein the step of identifying the number of parameters further includes the step of determining a standard deviation of the turbulence.

72. The method of claim 64, wherein the step of calculating the severity of the stenosis is accomplished with a feedforward neural network.

73. The method of claim 64, wherein the step of calculating the severity of the stenosis is accomplished with a feedback neural network.

74. The method of claim 64, wherein the step of identifying the number of parameters further includes the step of determining a second moment of intensity along the longitudinal axis of the signal void.

75. The method of claim 64, wherein the step of calculating the severity of the stenosis is accomplished with a traditional multivariate nonlinear regression.

76. The method of claim 64, wherein the step of calculating the severity of the stenosis is accomplished with a principal component analysis.

77. The method of claim 64, wherein the step of calculating the severity of the stenosis is accomplished with a discriminant analysis.

78. A system for determining a severity of a stenosis in a blood vessel depicted in a magnetic resonance imaging (MRI) data set, comprising:

a neural network configured to calculate the severity of the stenosis in the blood vessel based upon a number of input parameters;

the input parameters including at least one characteristic of a signal void associated with the stenosis in the MRI data set; and a signal void analyzer configured to identify the characteristic of the signal void in the MRI set, the signal void analyzer configured to determine a longitudinal axis of the signal void, the signal void analyzer configured to determine an average image intensity along the longitudinal axis of the signal void, the signal void analyzer configured to determine a presence of phase misregistration artifact.

79. A system for determining a severity of a stenosis in a blood vessel depicted in a magnetic resonance imaging (MRI) data set, comprising:

a neural network configured to calculate the severity of the stenosis in the blood vessel based upon a number of input parameters;

the input parameters including at least one characteristic of a signal void associated with the stenosis in the MRI data set; and a signal void analyzer configured to identify the characteristic of the signal void in the MRI set, the signal void analyzer configured to determine a longitudinal axis of the signal void, the signal void analyzer configured to determine a flow rate of blood through the blood vessel.

80. A system for determining a severity of a stenosis in a blood vessel depicted in a magnetic resonance imaging (MRI) data set, comprising:

a neural network configured to calculate the severity of the stenosis in the blood vessel based upon a number of input parameters;

the input parameters including at least one characteristic of a signal void associated with the stenosis in the MRI data set; and a signal void analyzer configured to identify the characteristic of the signal void in the MRI set, the signal void analyzer configured to determine an average image intensity along a longitudinal axis of the signal void, the signal void analyzer configured to determine a flow rate of blood through the blood vessel.

* * * * *

UNITED STATES PATENT AND TRADEMARK OFFICE
CERTIFICATE OF CORRECTION

PATENT NO. : 6,377,832 B1
DATED : April 23, 2002
INVENTOR(S) : Bergman et al.

It is certified that error appears in the above-identified patent and that said Letters Patent is hereby corrected as shown below:

Column 3,
Line 23, after "vessel", delete "109" and replace it with -- 103 --
Line 25, after "flow," delete "103" and replace it with -- 109 --

Column 6,
Line 3, delete "316 (FIG. 3)" and replace it with -- 216 (FIG. 2) --

Signed and Sealed this

Twenty-ninth Day of October, 2002

Attest:

Attesting Officer

JAMES E. ROGAN
Director of the United States Patent and Trademark Office